United States Patent
Zhong et al.

(10) Patent No.: US 11,125,498 B1
(45) Date of Patent: Sep. 21, 2021

(54) GAS LIQUEFACTION SEPARATOR, GAS LIQUEFACTION RECOVERY SYSTEM, AND METHOD FOR SEPARATING AND RECOVERING ETHYLENE OXIDE

(71) Applicants: Chio Kang Medical, Inc, Palo Alto, CA (US); QIAOKANG BIOTECH (GUANGDONG) CO., LTD., Guangzhou (CN)

(72) Inventors: Xiuling Zhong, Guangzhou (CN); Jianlong Xue, Guangzhou (CN); Dongxin Hou, Guangzhou (CN); Jiali Lin, Guangzhou (CN); Yecheng He, Guangzhou (CN); Shengwei Hu, Guangzhou (CN); Ziping Zhu, Guangzhou (CN); Qinghua Xiao, Guangzhou (CN); Lixiong Feng, Palo Alto, CA (US)

(73) Assignees: Chio Kang Medical, Inc., Palo Alto, CA (US); Qiaokane Biotech (Guangdong) Co., LTD., Guangzhou (CN)

( * ) Notice: Subject to any disclaimer, the term of this patent is extended or adjusted under 35 U.S.C. 154(b) by 0 days.

(21) Appl. No.: 17/002,529

(22) Filed: Aug. 25, 2020

Related U.S. Application Data (63) Continuation of application No. PCT/CN2020/100115, filed on Jul. 3, 2020.

(30) Foreign Application Priority Data

| Mar. 18, 2020 | (CN) | 202010190375.4 |
| Mar. 18, 2020 | (CN) | 202010190385.8 |

(Continued)

(51) Int. Cl.
  *F25J 3/06* (2006.01)
  *A61L 2/26* (2006.01)
  (Continued)

(52) U.S. Cl.
  CPC ............... *F25J 3/063* (2013.01); *A61L 2/206* (2013.01); *A61L 2/26* (2013.01); *C07D 301/32* (2013.01);
  (Continued)

(58) Field of Classification Search
  CPC ........ A61L 2/206; A61L 2/26; A61L 2101/38; C07D 301/32; F25J 3/063; F25J 2205/02
  See application file for complete search history.

(56) References Cited

U.S. PATENT DOCUMENTS

| 1,954,056 A | 4/1934 | Miller |
| 2,586,670 A | 2/1952 | Lambertsen |

(Continued)

FOREIGN PATENT DOCUMENTS

| CN | 1223166 A | 7/1999 |
| CN | 1397474 A | 2/2003 |

(Continued)

OTHER PUBLICATIONS

International Application No. PCT/CN2020/101140 as prepared by the Chinese International Searching Authority filed on Jul. 9, 2020, 59 pages.

(Continued)

*Primary Examiner* — Sean E Conley
(74) *Attorney, Agent, or Firm* — Adsero IP (57) ABSTRACT

The present disclosure provides a gas liquefaction separator, a gas liquefaction recovery system, and a method for separating and recovering ethylene oxide. The gas liquefaction separator includes a housing, a blocking plate, a gas baffle, and a liquid collector, the latter three being located inside the (Continued)

housing. The liquid collector—an outer edge of which is connected to an inner wall of the housing—is located below the gas baffle, which is located below the blocking plate. The liquid collector includes a first flow guide surface, on a bottom portion of which is disposed a first hole. The gas baffle—an upper surface of which forms a second flow guide surface and an outer edge of which has a protrusion(s)—is connected to the first flow guide surface through the protrusion(s), thereby forming a second hole between the outer edge of the gas baffle and the first flow guide surface.

7 Claims, 6 Drawing Sheets (30) Foreign Application Priority Data

| Mar. 18, 2020 | (CN) | ......................... 202020340493.4 |
| Mar. 18, 2020 | (CN) | ......................... 202020340598.X |
| Mar. 19, 2020 | (CN) | ......................... 202010194457.6 |
| Mar. 19, 2020 | (CN) | ......................... 202020348776.3 |

(51) Int. Cl.
*A61L 2/20* (2006.01)
*C07D 301/32* (2006.01)
*A61L 101/38* (2006.01)

(52) U.S. Cl.
CPC ......... *F25J 3/0695* (2013.01); *A61L 2101/38* (2020.08); *F25J 2205/02* (2013.01)

(56) References Cited

U.S. PATENT DOCUMENTS

| 2,817,689 | A |  | 12/1957 | White |
| 3,022,054 | A |  | 2/1962 | Kotzebue |
| 3,598,543 | A |  | 6/1969 | Crosby et al. |
| 3,572,391 | A |  | 3/1971 | Hirsch et al. |
| 3,844,739 | A |  | 10/1974 | Alfrey, Jr. |
| 3,961,920 | A |  | 6/1976 | Gilbert |
| 3,997,633 | A |  | 12/1976 | Leva et al. |
| 4,112,054 | A |  | 9/1978 | Feingold et al. |
| 4,119,539 | A |  | 10/1978 | Ettel et al. |
| 4,134,425 | A |  | 1/1979 | Gussefeld et al. |
| 4,243,636 | A |  | 1/1981 | Shiraki et al. |
| 4,301,113 | A |  | 11/1981 | Alguire et al. |
| 4,517,167 | A |  | 5/1985 | Popescu et al. |
| 4,549,363 | A |  | 10/1985 | Buonicore |
| 4,555,251 | A |  | 11/1985 | Jonsson |
| 4,831,196 | A |  | 5/1989 | Buonicore et al. |
| 5,084,075 | A |  | 1/1992 | Sircar |
| 5,204,075 | A |  | 4/1993 | Jain et al. |
| 5,270,000 | A |  | 12/1993 | Goldner et al. |
| 5,283,035 | A | * | 2/1994 | Karthaus ................ A61L 2/206 422/31 |
| 5,290,345 | A |  | 3/1994 | Osendorf et al. |
| 5,511,409 | A |  | 4/1996 | Knaebel |
| 5,522,808 | A |  | 6/1996 | Skalla |
| 5,607,652 | A |  | 3/1997 | Hellmuth et al. |
| 5,641,455 | A |  | 6/1997 | Rosenlund et al. |
| 5,702,669 | A |  | 12/1997 | Green et al. |
| 5,741,470 | A |  | 4/1998 | Wenzler |
| 5,755,857 | A |  | 5/1998 | Acharya et al. |
| 5,779,773 | A |  | 7/1998 | Cam et al. |
| 5,964,927 | A |  | 10/1999 | Graham et al. |
| 6,156,101 | A |  | 12/2000 | Naheiri |
| 6,684,648 | B2 |  | 2/2004 | Faqih |
| 6,743,402 | B2 |  | 6/2004 | Shimakawa |
| 7,316,733 | B1 |  | 1/2008 | Hedrick |
| 7,625,535 | B2 |  | 12/2009 | Yamaguchi |
| 8,110,156 | B2 |  | 2/2012 | Ricciardi et al. |
| 8,431,085 | B2 |  | 4/2013 | Froderberg et al. |
| 9,616,143 | B2 |  | 4/2017 | Snyder et al. |
| 10,987,443 | B1 |  | 4/2021 | Hu et al. |
| 2002/0046569 | A1 |  | 4/2002 | Faqih |
| 2002/0197194 | A1 |  | 12/2002 | Machado et al. |
| 2005/0145108 | A1 |  | 7/2005 | Rubin |
| 2006/0236860 | A1 |  | 10/2006 | Sumida et al. |
| 2006/0249027 | A1 |  | 11/2006 | Adolphsen et al. |
| 2007/0209383 | A1 |  | 9/2007 | Hutton |
| 2008/0078289 | A1 |  | 4/2008 | Sergi et al. |
| 2008/0080999 | A1 |  | 4/2008 | Bondar |
| 2008/0289591 | A1 |  | 11/2008 | Tessier et al. |
| 2010/0196194 | A1 |  | 8/2010 | Voeten et al. |
| 2011/0265644 | A1 |  | 11/2011 | Swami et al. |
| 2011/0283885 | A1 |  | 11/2011 | Thiele |
| 2012/0031268 | A1 |  | 2/2012 | Yaghi et al. |
| 2012/0298207 | A1 |  | 11/2012 | Woelk et al. |
| 2014/0119989 | A1 |  | 5/2014 | Hayashi |
| 2014/0251130 | A1 |  | 9/2014 | Sprinkle et al. |
| 2014/0290162 | A1 |  | 10/2014 | Tanimoto |
| 2016/0010883 | A1 |  | 1/2016 | Jomitz et al. |
| 2017/0056813 | A1 |  | 3/2017 | McMahon et al. |
| 2019/0076776 | A1 |  | 3/2019 | Mahecha-Botero et al. |
| 2019/0151791 | A1 |  | 5/2019 | Awadh et al. |
| 2019/0175971 | A1 |  | 6/2019 | Moore et al. |
| 2020/0148655 | A1 | * | 5/2020 | Duff .................... C07D 301/32 |

FOREIGN PATENT DOCUMENTS

| CN | 101224381 | A | 7/2008 |
| CN | 101549241 | A | 10/2009 |
| CN | 101773762 | A | 7/2010 |
| CN | 201632182 | U | 11/2010 |
| CN | 102173384 | A | 9/2011 |
| CN | 102219642 | A | 10/2011 |
| CN | 102302791 | A | 1/2012 |
| CN | 102921570 | A | 2/2013 |
| CN | 202802975 | U | 3/2013 |
| CN | 202933710 | U | 5/2013 |
| CN | 203183363 | U | 9/2013 |
| CN | 103386141 | A | 11/2013 |
| CN | 103394109 | A | 11/2013 |
| CN | 103394278 | A | 11/2013 |
| CN | 103657383 | A | 3/2014 |
| CN | 103706233 | A | 4/2014 |
| CN | 203507806 | U | 4/2014 |
| CN | 203564952 | U | 4/2014 |
| CN | 103800926 | A | 5/2014 |
| CN | 103908688 | A | 7/2014 |
| CN | 203749877 | U | 8/2014 |
| CN | 203750388 | U | 8/2014 |
| CN | 203750389 | U | 8/2014 |
| CN | 104014227 | A | 9/2014 |
| CN | 104275085 | A | 1/2015 |
| CN | 104307008 | A | 1/2015 |
| CN | 204261680 | U | 4/2015 |
| CN | 204447972 | U | 7/2015 |
| CN | 104815535 | A | 8/2015 |
| CN | 105132060 | A | 12/2015 |
| CN | 105327665 | A | 2/2016 |
| CN | 105664822 | A | 2/2016 |
| CN | 205300112 | U | 6/2016 |
| CN | 210721130 | U | 6/2016 |
| CN | 106139199 | A | 11/2016 |
| CN | 106421844 | A | 2/2017 |
| CN | 106475021 | A | 3/2017 |
| CN | 106582126 | A | 4/2017 |
| CN | 206443946 | U | 8/2017 |
| CN | 206535551 | U | 10/2017 |
| CN | 206853397 | U | 1/2018 |
| CN | 107677016 | A | 2/2018 |
| CN | 207169397 | U | 4/2018 |
| CN | 207187436 | U | 4/2018 |
| CN | 207356290 | U | 5/2018 |
| CN | 207745676 | U | 8/2018 |
| CN | 207913454 | U | 9/2018 |
| CN | 108607511 | A | 10/2018 |
| CN | 208047841 | U | 11/2018 |
| CN | 208218734 | U | 12/2018 |
| CN | 109382064 | A | 2/2019 |
| CN | 208448985 | U | 2/2019 |

(56) References Cited

FOREIGN PATENT DOCUMENTS

| CN | 208893903 U | 5/2019 |
|---|---|---|
| CN | 110145747 A | 8/2019 |
| CN | 110302634 A | 10/2019 |
| CN | 110404485 A | 11/2019 |
| CN | 110461371 A | 11/2019 |
| CN | 209662917 U | 11/2019 |
| CN | 110833754 A | 2/2020 |
| CN | 210021633 U | 2/2020 |
| CN | 210088451 U | 2/2020 |
| DE | 4236622 C1 | 3/1994 |
| EP | 0130319 A2 | 1/1985 |
| EP | 0350677 A1 | 1/1990 |
| EP | 1302478 A1 | 4/2003 |
| EP | 2883598 A1 | 6/2015 |
| GB | 1472091 A | 4/1977 |
| JP | 2008114210 A | 5/2008 |
| JP | 2013172790 A | 10/2016 |
| JP | 2010259648 A | 5/2018 |
| WO | WO2011002277 A1 | 1/2011 |
| WO | WO-2019-136504 A1 | 7/2019 |
| WO | WO2019236249 A1 | 12/2019 |

OTHER PUBLICATIONS

U.S. Appl. No. 17/012,857, TrackOne Bypass CON Application filed Sep. 4, 2020, 148 pages.
International Application No. PCT/CN2020/100143 as prepared by the Chinese International Searching Authority filed on Jul. 3, 2020, 25 pages.
U.S. Appl. No. 17/002,500, TrackOne Bypass CON Application filed Aug. 25, 2020, 61 pages.
International Application No. PCT/CN2020/100125 as prepared by the Chinese International Searching Authority filed on Jul. 3, 2020, 27 pages.
U.S. Appl. No. 17/002,523, TrackOne Bypass CON Application filed Aug. 25, 2020, 72 pages.
U.S. Appl. No. 17/002,523 Non-Final Office Action, dated Oct. 27, 2020, 54 pages.
International Application No. PCT/CN2020/100115 as prepared by the Chinese International Searching Authority filed on Jul. 3, 2020, 22 pages.
International Application No. PCT/CN2020/100119 as prepared by the Chinese International Searching Authority filed on Jul. 3, 2020, 29 pages.
U.S. Appl. No. 17/002,540, TrackOne Bypass CON Application filed Aug. 25, 2020, 89 pages.
International Application No. PCT/CN2020/100120 as prepared by the Chinese International Searching Authority filed on Jul. 3, 2020, 28 pages.
U.S. Appl. No. 17/004,730, TrackOne Bypass CON Application filed Aug. 27, 2020, 77 pages.
International Application No. PCT/CN2020/101142 as prepared by the Chinese International Searching Authority filed on Jul. 9, 2020, 29 pages.
U.S. Appl. No. 17/012,864, TrackOne Bypass CON Application filed Sep. 4, 2020, 78 pages.
International Application No. PCT/CN2020/100144 as prepared by the Chinese International Searching Authority filed on Jul. 3, 2020, 24 pages.
U.S. Appl. No. 17/004,903, TrackOne Bypass CON Application filed Aug. 27, 2020, 67 pages.
U.S. Appl. No. 17/004,903 Notice of Allowance, dated Nov. 6, 2020, 19 pages.
International Application No. PCT/CN2020/100122 as prepared by the Chinese International Searching Authority filed on Jul. 3, 2020, 34 pages.
U.S. Appl. No. 17/004,930, TrackOne Bypass CON Application filed Aug. 27, 2020, 80 pages.
U.S. Appl. No. 17/004,930 Office Action-Restriction Requirement, dated Nov. 4, 2020, 6 pages.
International Application No. PCT/CN2020/100113 as prepared by the Chinese International Searching Authority filed on Jul. 3, 2020, 35 pages.
U.S. Appl. No. 17/004,971, TrackOne Bypass CON Application filed Aug. 27, 2020, 75 pages.
U.S. Appl. No. 17/012,857, Non-Final Office Action, dated Nov. 24, 2020, 13 pages.
U.S. Appl. No. 17/002,540, Office Action-Restriction Requirement, dated Dec. 1, 2020, 7 pages.
U.S. Appl. No. 17/002,500, Non-Final Office Action dated Dec. 8, 2020, 109 pages.
Kahm et al., 2018 "Lyapunov exponents with Model Predictive Control for exothermic batch reactors" IFAC-PapersOnline, 51, 417-422.
U.S. Appl. No. 17/004,971, Office Action-Restriction Requirement, dated Dec. 9, 2020, 6 pages.
U.S. Appl. No. 17/002,523 Notice of Allowance, dated Dec. 17, 2020, 35 pages.
U.S. Appl. No. 17/004,930 Office Action-Restriction Requirement, dated Dec. 18, 2020, 8 pages.
U.S. Appl. No. 17/002,540, Non-Final Office Action dated Dec. 30, 2020, 62 pages.
U.S. Appl. No. 17/004,930 Non-Final Office Action dated Jan. 26, 2021, 28 pages.
International Search Report and Written Opinion, International Application No. PCT/CN2020/101140 dated Dec. 21, 2020, 11 pages.
International Search Report and Written Opinion, International Application No. PCT/CN2020/100143 dated Dec. 21, 2020, 9 pages.
International Search Report and Written Opinion, International Application No. PCT/CN2020/100125 dated Dec. 23, 2020, 9 pages.
International Search Report and Written Opinion, International Application No. PCT/CN2020/100115 dated Dec. 16, 2020, 11 pages.
International Search Report and Written Opinion, International Application No. PCT/CN2020/100119 dated Dec. 17, 2020, 9 pages.
International Search Report and Written Opinion, International Application No. PCT/CN2020/101142 dated Dec. 16, 2020, 11 pages.
International Search Report and Written Opinion, International Application No. PCT/CN2020/100144 dated Dec. 18, 2020, 10 pages.
U.S. Appl. No. 17/002,500, Final Office Action dated Feb. 8, 2021, 57 pages.
U.S. Appl. No. 17/004,971, Notice of Allowance, dated Feb. 8, 2021, 30 pages.
U.S. Appl. No. 17/012,857, Notice of Allowance, dated Mar. 1, 2021, 26 pages.
U.S. Appl. No. 17/002,540, Final Office Action, dated on Mar. 26, 2021, 36 pages.
U.S. Appl. No. 17/004,730, Non-Final Office Action, dated Apr. 1, 2021, 30 pages.
U.S. Appl. No. 17/002,500, Non-Final Office Action dated Apr. 14, 2021, 89 pages.
U.S. Appl. No. 17/002,540, Notice of Allowance, dated on Apr. 26, 2021, 21 pages.
International Search Report & Written Opinion for PCT/CN2020/100113 as prepared by the Chinese International Searching Authority dated Mar. 31, 2021, 10 pages.
International Search Report & Written Opinion for PCT/CN2020/100122 as prepared by the Chinese International Searching Authority dated Mar. 26, 2021, 11 pages.
International Search Report & Written Opinion for PCT/CN2020/100120 as prepared by the Chinese International Searching Authority dated Mar. 31, 2021, 10 pages.
U.S. Appl. No. 17/004,930 Notice of Allowance, dated Apr. 28, 2020, 35 pages.
U.S. Appl. No. 17/004,903 Notice of Allowance, dated May 17, 2021, 20 pages.

(56) References Cited

OTHER PUBLICATIONS

U.S. Appl. No. 17/002,523 Notice of Allowance, dated May 27, 2021, 26 pages.
U.S. Appl. No. 17/012,864, Notice of Allowance, dated Jun. 15, 2021, 56 pages.
U.S. Appl. No. 17/004,730, Notice of Allowance, dated Jun. 24, 2021, 30 pages.
U.S. Appl. No. 17/012,857, Notice of Allowance, dated Jun. 28, 2021, 21 pages.
U.S. Appl. No. 17/002,500, Notice of Allowance dated Jul. 8, 2021, 27 pages.

* cited by examiner

GAS LIQUEFACTION SEPARATOR, GAS LIQUEFACTION RECOVERY SYSTEM, AND METHOD FOR SEPARATING AND RECOVERING ETHYLENE OXIDE

CROSS-REFERENCE TO RELATED PATENT APPLICATIONS

This application is a continuation of International Application No. PCT/CN2020/100115, filed on Jul. 3, 2020, which claims the benefit of Chinese Patent Application No. CN202010190385.8 filed on 18 Mar. 2020, Chinese Patent Application No. CN202010194457.6 filed on 19 Mar. 2020, Chinese Patent Application No. CN202020348776.3 filed on 19 Mar. 2020, Chinese Patent Application No. CN202010190375.4 filed on 18 Mar. 2020, Chinese Patent Application No. CN202020340598.X filed on 18 Mar. 2020, and Chinese Patent Application No. CN202020340493.4 filed on 18 Mar. 2020, the entire content of each of which is incorporated herein by reference in its entirety for all purposes.

TECHNICAL FIELD

The present disclosure relates to the technical field of sterilization technology, and more particularly, to a gas liquefaction separator, a gas liquefaction recovery system, and a method for separating and recovering ethylene oxide.

BACKGROUND

Ethylene oxide ("EO") is a broad-spectrum, high-efficiency sterilization agent with excellent sterilization performance. EO has strong penetrating power, can kill various microorganisms at normal room temperature, and does not damage the sterilized items during sterilization. Currently, the ethylene oxide gas sterilization method is one of the most important low-temperature sterilization methods, and is most commonly used in hospitals.

However, ethylene oxide itself is toxic, flammable, and explosive. After sterilization with the ethylene oxide gas, the sterilization exhaust gas generated in the sterilizer needs to receive a harmless gas treatment before being discharged. At present, the treatment methods of the ethylene oxide sterilization exhaust gas include one of: (1) Catalytic combustion method; (2) Absorption method; or (3) Low temperature recovery method. In the (1) Catalytic combustion method, the sterilization exhaust gas is converted to a non-toxic substance by catalytic combustion. However, since ethylene oxide is flammable and explosive, this method has potential safety hazards during the treatment of the sterilization exhaust gas. In the (2) Absorption method, the sterilization exhaust gas generates ethylene glycol by acid catalysis, and this method is suitable for the treatment of the high-concentration ethylene oxide exhaust gas. However, if the treatment operation is improperly performed, it may cause secondary pollution. In the (3) Low temperature recovery method, the sterilization exhaust gas is condensed at −29° C. to recover the ethylene oxide. However, this method has high energy consumption and very high equipment requirements.

Hence, there is a need for more robust and scalable solutions for implementing sterilization technologies, and, more particularly, for implementing a gas liquefaction separator, a gas liquefaction recovery system, and a method for separating and recovering ethylene oxide.

SUMMARY

The present disclosure provides a gas liquefaction separator including a housing, a blocking plate, a gas baffle, and a liquid collector, the latter three being located in the housing. The housing comprises a gas outlet located on a top portion of the housing, a gas inlet disposed on an inner side wall of the housing, and a liquid outlet located on a bottom portion of the housing. The blocking plate extends downward from a top wall of an inner cavity of the housing, wherein the gas inlet faces the blocking plate. The gas baffle is located below the blocking plate. The liquid collector is located below the gas baffle, and an outer edge of the liquid collector is connected to the inner side wall of the housing. The liquid collector includes a first flow guide surface. A first hole is disposed on the bottom portion of the first flow guide surface, an upper surface of the gas baffle forms a second flow guide surface, and an outer edge of the gas baffle has at least one protrusion. The gas baffle is connected to the first flow guide surface through the at least one protrusion, thereby forming a second hole between the outer edge of the gas baffle and the first flow guide surface.

The present disclosure further provides a gas liquefaction recovery system, including the above-mentioned gas liquefaction separator, and further including a gas intake pipe, a liquid storage tank, a gas extraction device, and a pressurization device. The gas inlet is connected to the gas intake pipe. The gas extraction device and the pressurizing device are disposed on the gas intake pipe.

The pressurizing device is disposed at a downstream side of the gas extraction device in a gas flow direction. The gas extraction device is configured to drive a gas to be separated into the gas liquefaction separator through the gas intake pipe, the pressurization device being configured to increase a gas pressure in the gas liquefaction separator. The liquid outlet is connected to the liquid storage tank.

The present disclosure further provides a method for separating and recovering ethylene oxide, which is performed by using the above-mentioned gas liquefaction separator, and the method includes:

S102, transporting a gas to be separated containing ethylene oxide into the gas liquefaction separator through the gas inlet by a gas extraction device of a gas liquefaction recovery system;

S104, pressurizing an inner cavity of the housing of the gas liquefaction separator by a pressurization device to allow the ethylene oxide in the gas to be separated in the gas liquefaction separator to be compressed and liquefied, thereby obtaining a liquid ethylene oxide and a residual gas;

S106, discharging the residual gas through the gas outlet; and

S108, collecting the liquid ethylene oxide from the liquid outlet.

The gas liquefaction separator, the gas liquefaction recovery system, and the method for separating and recovering ethylene oxide provided by the present disclosure have the following beneficial effects:

1. The gas liquefaction separator has a simple structure and can be used for the compression, liquefaction, and gas-liquid separation of the ethylene oxide exhaust gas. When used, the gas liquefaction separator reduces the difficulty of the recovery and treatment for the ethylene oxide exhaust gas.

2. The gas liquefaction recovery system is simple to be assembled, can be cooperatively used with a sterilizer, can directly perform the compression, liquefaction, and gas-liquid separation on the sterilization exhaust gas generated by the sterilizer, and does not require the exhaust gas collection process, the transportation process, and the like, which reduces the difficulty of the recovery and treatment for the ethylene oxide sterilization exhaust gas, and improves the safety of the treatment.

3. The method for separating and recovering ethylene oxide has simple operational steps and can be performed at normal room temperature, which allows the ethylene oxide to be recovered efficiently, while reducing the recovery costs and protecting the environment.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

DETAILED DESCRIPTION OF THE EMBODIMENTS

Exemplary embodiments will be described hereafter with reference to the drawings to clearly and fully illustrate the technical solutions of the present disclosure. All other embodiments obtained by a person of ordinary skill in the art based on the embodiments in the present disclosure without creative efforts are within the scope of the present disclosure.

The following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

As shown in FIGS. 1 to 4, the present disclosure provides an embodiment of a gas liquefaction separator 1. The gas liquefaction separator 1 may include, without limitation, a housing 2, a blocking plate 4, a gas baffle 6, and a liquid collector 7, and the like.

Figure 1A:
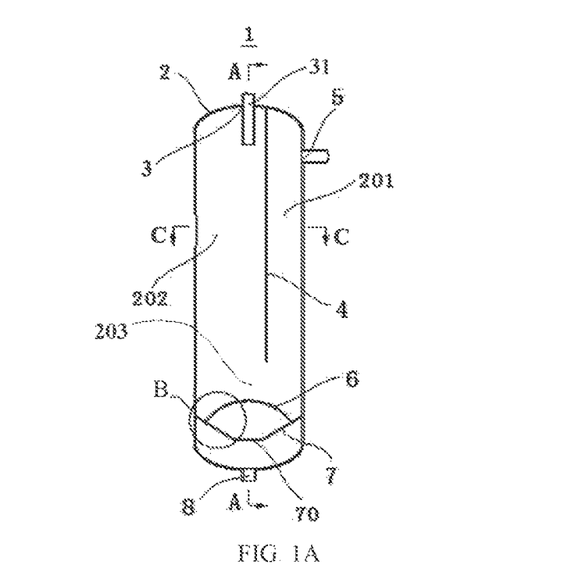
FIG. 1A is a schematic structural view of a gas liquefaction separator provided by an embodiment of the present disclosure.
Figure 1B:
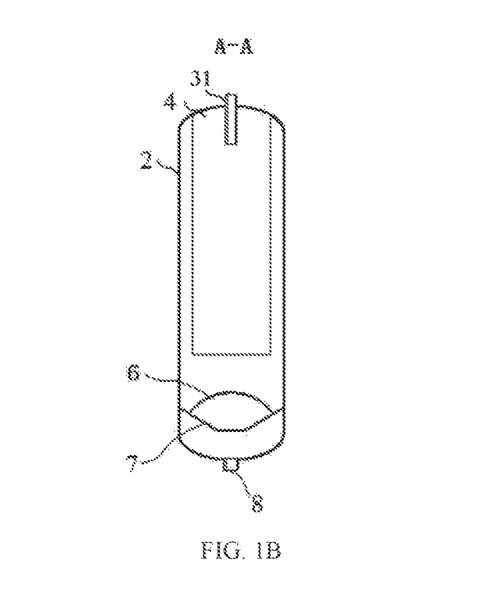
FIG. 1B is a cross-sectional view taken along line A-A of FIG. 1A.
Figure 1C:
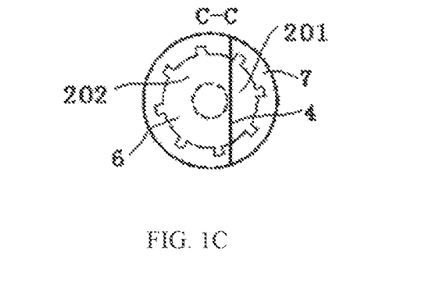
FIG. 1C is a cross-sectional view taken along line C-C of FIG. 1A.

The housing 2 may include, but is not limited to, a gas outlet 3, a gas inlet 5, and a liquid outlet 8, and the like. The housing 2 may include, for example, a vertical cylindrical tank. The gas outlet 3 may be disposed on a top portion of the housing 2. The gas inlet 5 may be located on an upper portion of the side of the housing 2, and may be disposed adjacent to the top portion of the housing 2. The liquid outlet 8 may be disposed on a bottom portion of the housing 2. The gas inlet 5 may be configured to input a gas to be separated, for example, ethylene oxide sterilization exhaust gas or the like. The gas liquefaction separator 1 can be used to separate a liquid ethylene oxide from the sterilization exhaust gas, and the separated liquid ethylene oxide may be discharged from the liquid outlet 8. It can be understood that the gas to be separated is not limited to ethylene oxide sterilization exhaust gas, and that the gas liquefaction separator 1 can also be used for the separation and recovery of other gases containing ethylene oxide or can be used for the separation and recovery of other gases (not containing ethylene oxide but) with properties similar to ethylene oxide.

The blocking plate 4, the gas baffle 6, and the liquid collector 7 may be disposed inside the housing 2. The gas baffle 6 may be located below the blocking plate 4, while the liquid collector 7 may be located below the gas baffle 6.

The blocking plate 4 may extend downward from a top wall of an inner cavity of the housing 2, and may divide the inner cavity of the housing 2 into an upstream chamber 201, a downstream chamber 202, and a lower chamber 203. The upstream chamber 201 and the downstream chamber 202 may be separated by the blocking plate 4, and the lower chamber 203 may be located below the blocking plate 4. A bottom portion of the upstream chamber 201 and a bottom portion of the downstream chamber 202 may be in fluid communication with each other through the lower chamber 203. The gas outlet 3 might correspond to the downstream chamber 202. The gas inlet 5 might correspond to the upstream chamber 201, and might be opposed to the blocking plate 4. The liquid outlet 8 might correspond to the lower chamber 203. The blocking plate 4 may be configured to block, or impede the flow of, the gas to be separated that enters through the gas inlet 5, to prevent the gas to be separated from being discharged from the housing 2 directly from the gas inlet 5 through the gas outlet 3.

A liquid substance formed from the gas to be separated in the gas liquefaction separator 1, such as liquid ethylene oxide, tends to adhere to the blocking plate 4, and then to condense together and to flow downward along the blocking plate 4 to fall from a lower edge of the blocking plate 4. This is beneficial to the recovery of liquid substances, such as the liquid ethylene oxide. In addition, providing the blocking plate 4 can increase the time period that the gas to be separated stays in the gas liquefaction separator 1, which is beneficial to the further liquefaction of the gas to be separated and beneficial to the improvement of the compression and recovery rate. Moreover, the blocking plate 4 can also prevent the liquefied ethylene oxide from being re-vaporized due to excessive gas flow.

In an embodiment, the blocking plate 4 may be deviated, or displaced, from the longitudinal axis of the housing 2. The size of the downstream chamber 202 may be larger than the size of the upstream chamber 201. The gas inlet 5 may be disposed on the inner side wall of the housing 2 that is adjacent to the blocking plate 4. Furthermore, the gas inlet 5 may be located on a side wall of the housing 2, and an axis of the gas inlet 5 may be perpendicular to a longitudinal axis of the housing 2. In one embodiment, the blocking plate 4 might be a flat plate that is parallel to the longitudinal axis of the housing 2. An upper edge of the blocking plate 4 may be connected to the top wall of the housing 2. The two side edges of the blocking plate 4 might be each connected to the inner side wall of the housing 2, and the lower edge of the blocking plate 4 might be located above the gas baffle 6. The gas outlet 3 and the gas inlet 5 may be located on opposite sides of the blocking plate 4. In some embodiments, the gas to be separated that enters the upstream chamber 201 from the gas inlet 5 can enter the downstream chamber 202 only through the lower chamber 203. In other embodiments, the blocking plate 4 can be disposed obliquely with respect to the longitudinal axis of the housing 2. In one embodiment, a surface of the blocking plate 4 facing the gas inlet 5 is an uneven surface, not a smooth surface, which is beneficial to the condensation of liquid drops.

Figure 2:
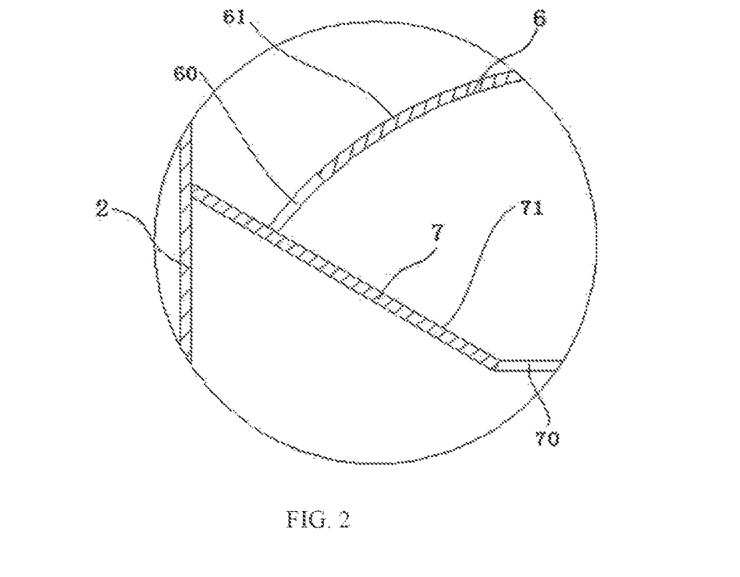
FIG. 2 is an enlarged view of area B in FIG. 1A.
Figure 4A:
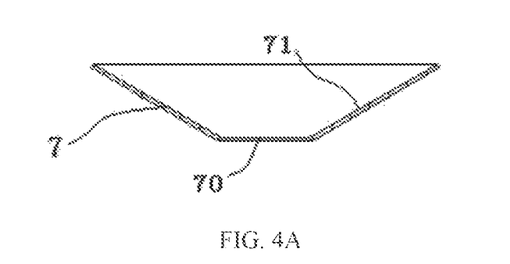
FIG. 4A is a schematic cross-sectional view of a liquid collector in FIG. 1A.
Figure 4B:
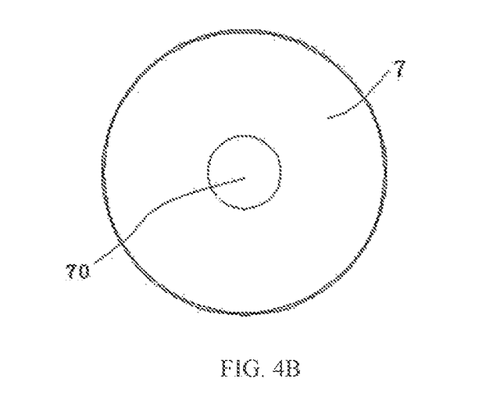
FIG. 4B is a schematic top view of the liquid collector in FIG. 4A.

Referring to FIGS. 2, 4A, and 4B, an outer edge of the liquid collector 7 may be connected to the inner side wall of the housing 2 by welding, for example. The liquid collector 7 might be configured to collect the condensed liquid. The liquid collector 7 may include, without limitation, a first flow guide surface 71 that is configured to collect the liquid and to cause the liquid to flow downward. The first flow guide surface 71 can have a truncated cone shape or a concave arc shape that protrudes downward. A bottom portion of the first flow guide surface 71 may be provided with a first hole 70, which is opposite to the liquid outlet 8. The liquid outlet 8 may be disposed below the first hole 70. The liquid can enter the liquid outlet 8 from the first hole 70. The diameter of the first hole 70 can be larger than the diameter of the liquid outlet 8. In this embodiment, the liquid collector 7 has a funnel shape, and an outer edge of a top portion of the liquid collector 7 may be connected to the inner side wall of the housing 2.

Figure 3A:
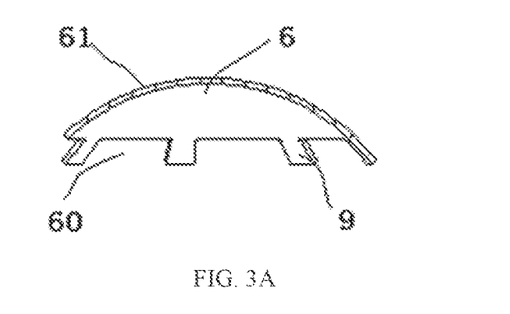
FIG. 3A is a schematic cross-sectional view of a gas baffle in FIG. 1A.
Figure 3B:
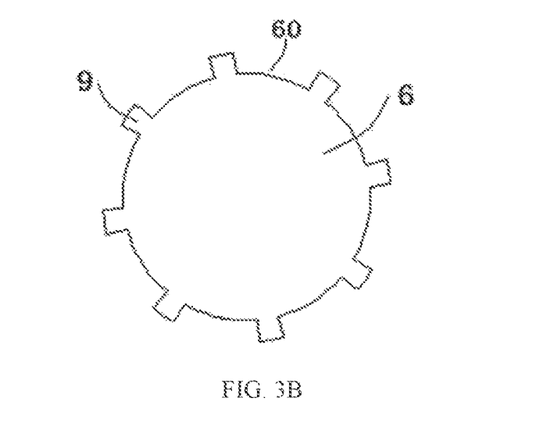
FIG. 3B is a schematic top view of the gas baffle in FIG. 3A.

Referring to FIGS. 3A and 3B, an upper surface of the gas baffle 6 may form a second flow guide surface 61. An outer edge of the gas baffle 6 may be connected to the first flow guide surface 71 of the liquid collector 7 through at least one protrusion 9 by welding, for example, thereby forming a second hole(s) 60 between the outer edge of the gas baffle 6 and the first flow guide surface 71. The second flow guiding surface 61 can block the downward flow of the gas above it, thereby avoiding the liquefied ethylene oxide liquid being flushed or even re-gasified due to a disturbance of liquid by the gas flow. The liquid that is condensed on the gas baffle 6 and the liquid that falls on the gas baffle 6 can flow to the second hole 60 along the second flow guide surface 61, can be discharged through the first hole 70 along the first flow guide surface 71, and can be discharged from the gas liquefaction separator 1 through the liquid outlet 8. The number of the at least one protrusion 9 can be two or more, and a plurality of protrusions 9 may be arranged uniformly and spaced apart from each other in a circumferential direction or along a circumference of the gas baffle 6, thereby forming a plurality of second holes 60 that are evenly distributed around the edge of the gas baffle 6. A middle portion of the second flow guiding surface 61 may be upwardly arched, and may have a shape with a higher middle portion and a lower edge, which is beneficial to guide the condensed liquid into the second hole(s) 60. The gas baffle 6 may have, for example, a convex arc-shaped plate, and a convex arc-shaped upper surface of the convex arc-shaped plate may form the second flow guide surface 61. In an embodiment, the gas baffle 6 may have a curved pot lid shape.

An exhaust pipe 31 may be further disposed in the gas outlet 3 and may extend inside the housing 2 through the top wall of the housing 2. Specifically, the exhaust pipe 31 may extend into the downstream chamber 202. In this way, the liquid ethylene oxide is prevented from being flushed out of the gas liquefaction separator 1 by the flow of the gas to be discharged.

Figure 5:
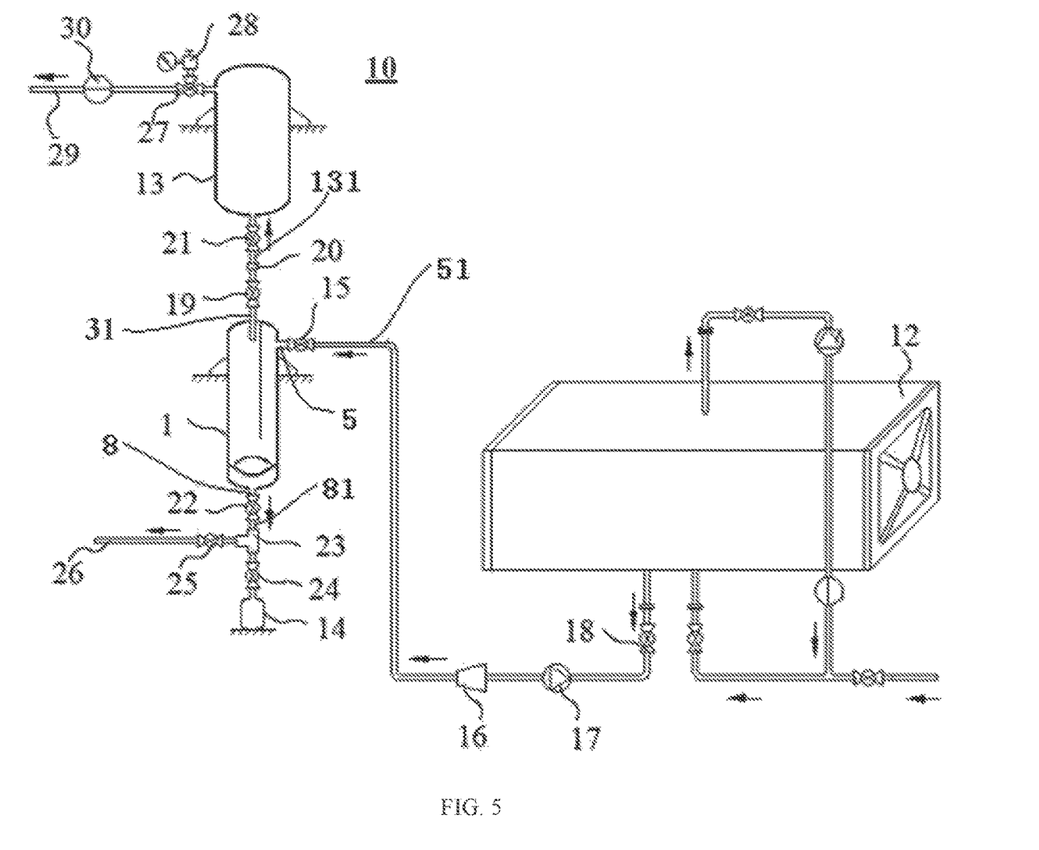
FIG. 5 is a schematic structural view of a gas liquefaction recovery system provided by an embodiment of the present disclosure.

Referring to FIG. 5, the present disclosure also provides an embodiment of a gas liquefaction recovery system 10, which includes the above-mentioned gas liquefaction separator 1.

In an embodiment, the gas liquefaction recovery system 10 might further include, without limitation, a gas intake pipe 51. The gas intake pipe 51 may be connected to the gas inlet 5. The gas intake pipe 51 may be configured to introduce the gas to be separated into the gas liquefaction separator 1. The liquid in the gas liquefaction separator 1 may be discharged through the liquid outlet 8, and the residual gas remaining after the treatment to the gas to be separated by the gas liquefaction separator 1 may be discharged through the gas outlet 3. In an embodiment, the gas liquefaction recovery system 10 may further include, but is not limited to, the exhaust pipe 31 connected to the gas outlet 3, and the residual gas may be discharged through the exhaust pipe 31. When the gas liquefaction recovery system 10 is used to recover liquid ethylene oxide from ethylene oxide sterilization exhaust gas, the gas intake pipe 51 may be, for example, connected to an ethylene oxide sterilizer 12. Of course, the gas liquefaction recovery system 10 can also be used for recovery of other mixed gases, and is not limited to the recovery of ethylene oxide.

In an embodiment, the gas liquefaction recovery system 10 may further include, but is not limited to, a first valve 18, a gas extraction device 17, and a pressurization device 16, which are disposed on the gas intake pipe 51. The gas extraction device 17 may be used to drive the gas to be separated into the gas liquefaction separator 1 through the gas intake pipe 51. The gas extraction device 17 can be a vacuum pump, or the like. The pressurization device 16 may be configured to increase the gas pressure in the gas liquefaction separator 1. The pressurizing device 16 may be disposed at the downstream side of the gas extraction device 17 in the gas flow direction. The pressurizing device 16 may be, for example, a booster pump, or the like. The first valve 18 may be disposed at the upstream side of the gas extraction device 17 in the gas flow direction. Furthermore, the gas liquefaction recovery system 10 may further include, without limitation, a second valve 15 through which the gas intake pipe 51 may be connected to the gas inlet 5.

In an embodiment, the gas liquefaction recovery system 10 may further include, but is not limited to, a drain pipe 81, or the like. The liquid outlet 8 may be connected to a liquid storage tank 14 through the drain pipe 81, and the liquid separated by the gas liquefaction separator 1 can be stored in the liquid storage tank 14. The liquid storage tank 14 may be used to store, for example, the liquid ethylene oxide. Alternatively or additionally, the liquid outlet 8 may be connected to the drain pipe 81 through a third valve 22. Alternatively or additionally, the drain pipe 81 may be connected to the liquid storage tank 14 through a fourth valve 24. Further alternatively or additionally, the drain pipe 81 may be further connected to a branch pipe 26, and a connection point between the branch pipe 26 and the drain pipe 81 may be located between the third valve 22 and the fourth valve 24. A fifth valve 25 may be also mounted on the branch pipe 26. The branch pipe 26 can be respectively connected to upper and lower portions of the drain pipe 81 through a three-way joint 23, or the like.

In addition, a seventh valve 19 may be mounted on the exhaust pipe 31. In addition, the gas liquefaction recovery system 10 can further include a gas storage tank 13. An input pipe 131 of the gas storage tank 13 can be connected to the exhaust pipe 31 through a two-way joint 20, or the like. An eighth valve 21 can be mounted on the input pipe 131. Furthermore, an output pipe of the gas storage tank 13 may be connected to a gas outtake pipe 29 through a sixth valve 27, and a gas concentration detector 30 may be mounted on the gas outtake pipe 29. A pressure sensor 28 may be mounted on the output pipe of the gas storage tank 13. The sixth valve 27 can be a three-way ball valve, or the like, and, in some embodiments, the pressure sensor 28 and the sixth valve 27 may be integrated as one member.

The above-mentioned valves can be electric valves in order to realize an automatic control of the gas liquefaction recovery system 10.

The embodiments of the present disclosure also provide a method for separating and recovering ethylene oxide, which is performed by using the above-mentioned gas liquefaction separator 1, and the method includes:

S102, transporting the gas to be separated containing ethylene oxide into the gas liquefaction separator 1 through the gas inlet 5 by the gas extraction device 17 of the gas liquefaction recovery system 10;

S104, pressurizing (the inner cavity of the housing 2 of) the gas liquefaction separator 1 by the pressurization device 16 to allow the ethylene oxide in the gas to be separated in the gas liquefaction separator 1 to be compressed and liquefied, thereby obtaining the liquid ethylene oxide and the residual gas;

S106, discharging the residual gas through the gas outlet 3; and

S108, collecting the liquid ethylene oxide from the liquid outlet 8.

In an embodiment, the gas to be separated is the ethylene oxide sterilization exhaust gas in the ethylene oxide sterilizer 12, and the gas extraction device 17 extracts the ethylene oxide sterilization exhaust gas from the ethylene oxide sterilizer 12 into the gas liquefaction separator 1.

According to some embodiments, the exhaust pipe 31 may be mounted on the gas outlet 3 of the gas liquefaction separator 1, and may extend into the downstream chamber 202. The residual gas may be discharged through the exhaust pipe 31.

In an embodiment, the method might further include repeating steps of S102, S104, S106, and S108 at least once.

Alternatively, the method might further include: collecting the liquid ethylene oxide that is discharged through the liquid outlet 8 in the liquid storage tank 14; and collecting the residual gas that is discharged through the gas outlet 3 in the gas storage tank 13.

In another embodiment, the method might include repeating steps of S102, S104, and S106 at least once before performing the step of S108.

When the gas liquefaction recovery system 10 provided by an embodiment of the present disclosure is applied to recover ethylene oxide in the ethylene oxide sterilization exhaust gas, the operation process may be as follows.

1. The first valve 18 may be checked to ensure that it is closed, and the mixed sterilization gas (for example, EO+N$_2$, or the like) may be input into the sterilizer 12 for sterilization.

2. After completing the sterilization, the first valve 18, the second valve 15, the seventh valve 19, the eighth valve 21, the third valve 22, and the fourth valve 24 are opened, the fifth valve 25 and the sixth valve 27 are closed, and the gas extraction device 17 may be activated to apply a vacuum pressure to the sterilizer 12, thereby allowing the ethylene oxide sterilization exhaust gas in the sterilizer 12 to enter the gas liquefaction separator 1 through the gas inlet 5. A vacuum pump is used to apply the vacuum pressure on sterilizer 12, preferably to a range from about −0.08 MPa to about −0.02 MPa, preferably to about −0.08 MPa.

3. The pressurizing device 16 may be turned on to pressurize the interior of the gas liquefaction separator 1, and the ethylene oxide sterilization exhaust gas may be allowed to be compressed and liquefied in the gas liquefaction separator 1. For example, the internal pressure of the gas liquefaction separator 1 may be increased to a range from about 0.6 MPa to about 0.9 MPa, preferably to about 0.8 MPa. At this time, most of the ethylene oxide may start to liquefy, and the gas-liquid mixture may be blocked (or the flow of the gas-liquid mixture may be impeded) by the blocking plate 4. A part of the liquid may condense on the blocking plate 4 or on the inner wall of the housing 2 and may flow down to the liquid collector 7. The liquid may pass through the first hole 70, through the liquid outlet 8, through the third valve 22, through the drain pipe 81, through the three-way joint 23, and through the fourth valve 24, to eventually flow into the liquid storage tank 14 for storage, so that the liquid may be recovered and stored for reuse at a later time. Using the booster pump to increase the internal pressure of the system may allow the ethylene oxide in the sterilization exhaust gas to be compressed and liquefied, which is beneficial to the separation of the liquid ethylene oxide in the gas liquefaction separator 1. The separated liquid ethylene oxide that is collected in the liquid storage tank 14 may have a high concentration, and can be recovered and reused. When the system is pressurized to allow the ethylene oxide to be compressed and liquefied, the temperature can be controlled at a range from about 20° C. to about 30° C., and the duration can be controlled at a range from about 5 min to about 10 min. Furthermore, the concentration of ethylene oxide in the ethylene oxide exhaust gas may range from about 15% vol to about 55% vol.

The residual gas may enter the gas storage tank 13 through the exhaust pipe 31, the seventh valve 19, the two-way joint 20, the input pipe 131, and the eighth valve 21, and can be discharged through the output pipe of the gas storage tank 13, the sixth valve 27, and the gas outtake pipe 29 to enter the next step for sequentially performing the harmless gas treatment.

The pressure sensor 28 can monitor and control the pressures in the gas storage tank 13, the gas liquefaction separator 1, and the liquid storage tank 14. The concentration detector 30 can monitor the concentration of ethylene oxide in the gas outtake pipe 29 in real time, which effectively ensures effective gas treatment.

The compression, liquefaction, gas-liquid separation, and collection of the liquid ethylene oxide and the residual gas can be performed 1 to 5 times sequentially, which can improve the compression and recovery rate of the ethylene oxide in the sterilization exhaust gas.

It can be understood that the booster pump and the vacuum pump can flexibly adjust the pressure in the gas liquefaction separator 1, which can not only introduce the ethylene oxide sterilization exhaust gas from the sterilizer 12 into the gas liquefaction separator 1, but can also achieve the effect of the compression and liquefaction by increasing the internal pressure of the gas liquefaction separator 1.

In addition, during compression and liquefaction, the third valve 22 and/or the fourth valve 24 may be closed, and the opening or closing of the fifth valve 25 can be controlled according to the circumstances. When the compression is completed, the third valve 22 and the fifth valve 25 may be opened, and the liquefied ethylene oxide can directly flow out through the branch pipe 26 to be reused.

In some embodiments, a gas liquefaction separator 1, a gas storage tank 13, and a liquid storage tank 14 may be combined to form the ethylene oxide sterilization exhaust gas recovery system 10, which may be used in conjunction with the sterilizer 12. By performing the compression, liquefaction, and gas-liquid separation for the ethylene oxide sterilization exhaust gas in the sterilizer 12, ethylene oxide with a high concentration can be recovered, resulting in the recovery efficiency of ethylene oxide being high. The gas liquefaction recovery system 10 has a simple structure and is easy to operate, which reduces the treatment difficulty of the ethylene oxide sterilization exhaust gas, and achieves the effects of saving resources, while reducing costs and protecting the environment. A plurality of valves may be provided in the present disclosure, which is beneficial to the disassembly, transportation, and maintenance of various assemblies.

Figure 6:
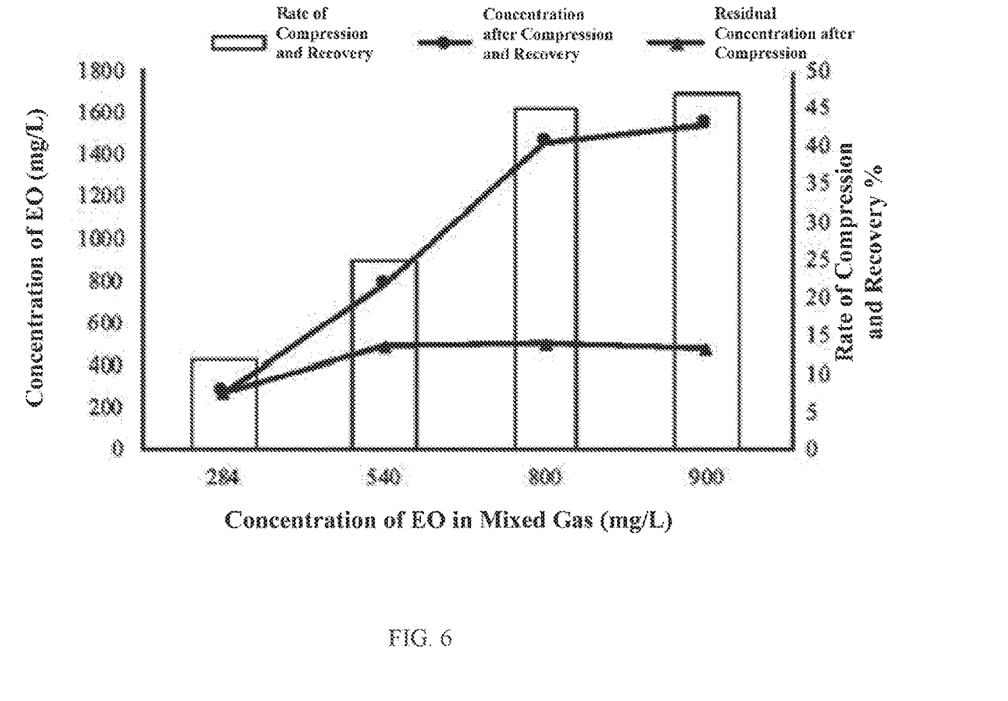
FIG. 6 is a graphical diagram illustrating detection results of a sterilization exhaust gas recovered by a method for separating and recovering ethylene oxide according to an embodiment of the present disclosure.

FIG. 6 shows detection results for recovering different ethylene oxide sterilization exhaust gases by the method for separating and recovering ethylene oxide according to an embodiment of the present disclosure.

The method for recovering the ethylene oxide sterilization exhaust gas may be as follows.

1. The sterilizer 12 may be set to a vacuum pressure of about −0.08 MPa to allow the ethylene oxide sterilization exhaust gas in the sterilizer 12 to enter the gas liquefaction separator 1 through the gas inlet 5.

2. The internal pressure of the gas liquefaction separator 1 may be increased to about 0.8 MPa by the booster pump to perform the compression and liquefaction.

3. The liquefied ethylene oxide may be discharged through the liquid outlet 8 of the gas liquefaction separator 1, the liquefied ethylene oxide may be flowed into the liquid storage tank 14 to be collected and recovered, and the recovery may be stopped when the internal pressure of the gas liquefaction separator 1 is decreased to about 0.7 MPa.

4. The residual gas from the gas liquefaction separator 1 may be input into the gas storage tank 13 for collection.

The concentrations of ethylene oxide in the four different types of ethylene oxide sterilization exhaust gases respectively are 284.6 mg/L, 540.4 mg/L, 788.3 mg/L, and 892.5 mg/L (corresponding to 284 mg/L, 540 mg/L, 800 mg/L, and 900 mg/L as denoted in the horizontal axis of FIG. 6, respectively). After recovery of the sterilization exhaust gas, the concentrations of ethylene oxide in the residual gases entering the gas storage tank 13 and the concentrations of ethylene oxide recovered in the liquid storage tank 14 are detected, and the detection results are shown in FIG. 6.

From the results in FIG. 6, it can be seen that the concentrations of EO in the residual gases (a mixture containing a small quantity of $EO+N_2$, or the like) detected by a gas chromatography detection system are 270.1 mg/L, 491.7 mg/L, 506.3 mg/L, and 480.4 mg/L, respectively. The concentrations of EO in the recovered liquid ethylene oxide are 277.2 mg/L, 790.1 mg/L, 1464.3 mg/L, and 1544.2 mg/L, respectively. The compression and recovery rates are 11.08%, 25.13%, 44.78%, and 47.22%, respectively. When the concentration of EO is 284 mg/L, the concentration before and after compression is substantially unchanged—that is, the mixed gas with a low-concentration of EO has a low compressibility at the pressure of about 0.8 MPa and is hard to be compressed. However, as the concentration of EO in the EO mixed gas increases, the purity and the recovery rate of the EO recovered by compression also increases.

Figure 7:
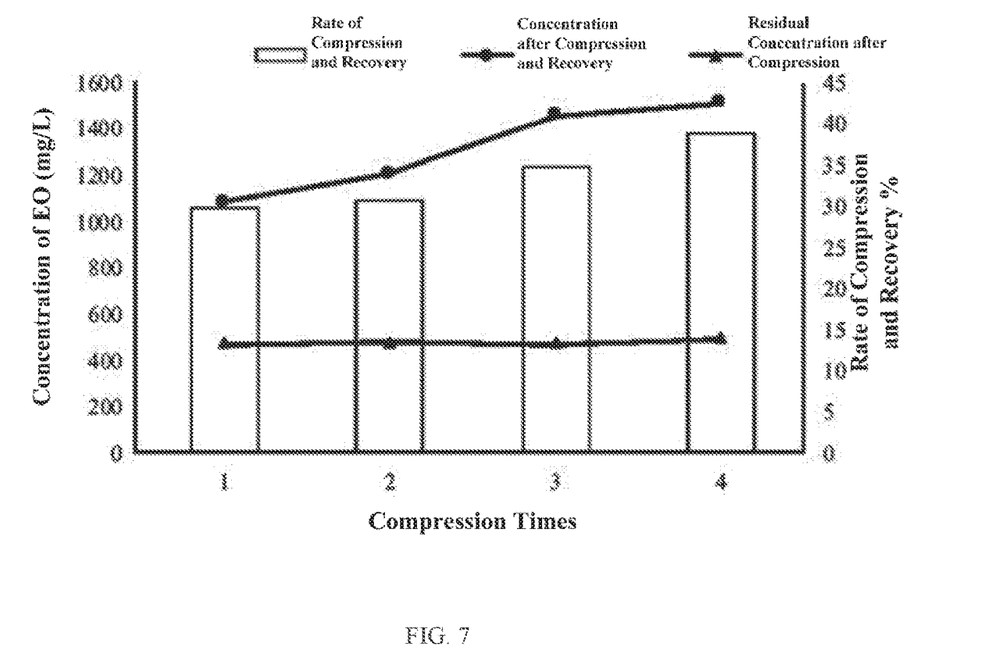
FIG. 7 is a graphical diagram illustrating detection results of a sterilization exhaust gas recovered by the method for separating and recovering ethylene oxide according to another embodiment of the present disclosure.

FIG. 7 shows detection results for recovering the ethylene oxide sterilization exhaust gases by the method for separating and recovering ethylene oxide according to another embodiment of the present disclosure.

The method for recovering the ethylene oxide sterilization exhaust gas may be as follows.

1. The sterilizer 12 may be set to a vacuum pressure of about −0.08 MPa to allow the ethylene oxide sterilization exhaust gas in the sterilizer 12 to enter the gas liquefaction separator 1 through the gas inlet 5. The concentration of ethylene oxide in the ethylene oxide exhaust gas might be about 788.3 mg/L.

2. The pressure of the gas liquefaction separator 1 may be increased by the booster pump to perform the compression and liquefaction, where the pressure might be about 0.8 MPa, the temperature might be about 20° C. to about 30° C., and the duration might be about 5 min to about 10 min.

3. The liquefied ethylene oxide may be discharged through the liquid outlet 8 of the gas liquefaction separator 1, the liquefied ethylene oxide may be flowed into the liquid storage tank 14 to be collected and recovered, and the recovery may be stopped when the internal pressure of the gas liquefaction separator 1 is decreased to about 0.7 MPa.

4. The residual gas in the gas liquefaction separator 1 may be input into the gas storage tank 13 for collection, and the collection of the residual gas in the gas storage tank 13 may be stopped when the internal pressure of the gas liquefaction separator 1 is decreased to about 0.6 MPa.

5. The above-mentioned steps may be repeated once, twice, or three times, or none of the above-mentioned steps may be repeated, to have multiple recovery operations for the sterilization exhaust gases. That is, in the process for recovering the ethylene oxide sterilization exhaust gases, the following steps each may be performed once, twice, three times, or four times in different embodiments: (a) the ethylene oxide sterilization exhaust gas in the sterilizer 12 may be injected into the gas liquefaction separator 1; (b) the internal pressure of the gas liquefaction separator 1 may be increased to about 0.8 MPa to perform the compression and liquefaction; (c) the liquefied ethylene oxide may be flowed into the liquid storage tank to be collected; (d) the recovery may be stopped when the pressure in the system is decreased to about 0.7 MPa; (e) the residue gas in the gas liquefaction separator 1 may be collected by the gas storage tank 13; and (f) the gas collection may be stopped when the pressure in the system is decreased to about 0.6 MPa.

After performing the above-mentioned steps once, twice, three times, or four times (corresponding to 1, 2, 3, or 4 on the horizontal axis of FIG. 7, respectively), the concentrations of ethylene oxide in the residual gases entering the gas storage tank 13 and the concentrations of ethylene oxide recovered in the liquid storage tank 14 are detected, and the results obtained are shown in FIG. 7.

From the results in FIG. 7, it can be seen that the concentrations of EO in the residual gases detected by the gas chromatography detection system respectively are 475.5 mg/L, 482.3 mg/L, 479.6 mg/L, and 499.2 mg/L. The concentrations of EO in the recovered liquid ethylene oxide respectively are 1092.4 mg/L, 1213.6 mg/L, 1463.3 mg/L, and 1518.2 mg/L. The compression and recovery rates respectively are 30.11%, 31.18%, 35.23%, and 39.11%. As the number of times that the compression and liquefaction is performed increases, the EO concentration of the recovered liquid ethylene oxide and the recovery rate increase rapidly, while the EO concentration of the residual gas in the gas storage tank 13 is substantially unchanged. In addition, for the exhaust gases with the same EO concentration compressed a different number of times under the same pressure, the EO concentration of the residual gas in the gas storage tank 13 after the compression and recovery is substantially the same, e.g., about 500 mg/L.

The present disclosure also provides the method for recovering the ethylene oxide sterilization exhaust gas using the gas liquefaction recovery system of the present embodiment.

1. The sterilizer 12 may be set to a vacuum pressure of about −0.08 MPa to allow the ethylene oxide sterilization exhaust gas in the sterilizer 12 to enter the gas liquefaction separator 1 through the gas inlet 5, wherein the concentration of ethylene oxide in the ethylene oxide sterilization exhaust gas might be about 788.3 mg/L.

2. The internal pressure of the gas liquefaction separator 1 may be increased to about 0.8 MPa by the booster pump to perform the compression and liquefaction, where the temperature might be about 20° C. to about 30° C., and the duration time might be about 5 min to about 10 min.

3. The residual gas from the gas liquefaction separator 1 may be input into the gas storage tank 13 for collection, collection of the residual gas may be stopped when the pressure is reduced to about 0.6 MPa, and the ethylene oxide exhaust gas from the sterilizer 12 may be introduced into the gas liquefaction separator 1 to increase the pressure of the gas liquefaction separator 1 for performing the compression and liquefaction.

4. Step 3 may be repeated about five times, and then the liquefied ethylene oxide may be discharged into the liquid storage tank 14 for recovery.

The concentration of ethylene oxide in the residual gas in the gas storage tank 13 and the concentration of ethylene oxide in the liquid ethylene oxide recovered in the liquid storage tank 14 may be detected. The EO concentration in the residual gas detected by the gas chromatography detection system is about 437.6 mg/L, while the EO concentration of the recovered liquid ethylene oxide is about 1616.5 mg/L, and the compression and recovery rate is about 32.22%.

The detection methods and conditions may be as follows:

1. Sampling may be performed through a sampling device and a composite membrane gas sampling bag in the detection.

2. Detecting the concentration of ethylene oxide in the ethylene oxide sterilization exhaust gas may be performed by the gas chromatography detection system, a non-limiting example of which may be as follows.

Instrument: Gas chromatograph Agilent 7890B;
Chromatography column: FFAP quartz capillary column (25 m×0.25 mm× 0.25 μm);
Temperature: column temperature maintained at 45° C. for 7 minutes, then increased the temperature to 120° C. at 15° C./min, and then maintained for 7 minutes, with the temperature at the sample inlet is 130° C., and the temperature at the detector being 150° C.;
Carrier gas: nitrogen 2 mL/min, hydrogen 35 mL/min, air 400 mL/min;
Sample introduction: automatic, gas sample 1 mL; and
Detector: hydrogen flame ionization detector ("FID").

3. Ethylene oxide concentration may be detected in real-time using a detector for online real-time detection of the concentration of the ethylene oxide gas in pipelines.

Instrument: online ethylene oxide concentration detector MIC-500s-ETO (0-99% vol, resolution 0.01% vol);
Fixed-type ethylene oxide alarm detector JSAS-ETO-AX (0-100 ppm, resolution 0.01 ppm); and
Online ethylene oxide concentration detector ("PID") (0-2000 ppm, resolution 0.1 ppm).

In summary, the gas liquefaction separator and the gas liquefaction recovery system provided by the present disclosure have the following beneficial effects:

1. The gas liquefaction separator has a simple structure, and can be used for the compression, liquefaction, and gas-liquid separation of the ethylene oxide sterilization exhaust gas, which can improve the compression and recovery rate, can obtain high-purity ethylene oxide, and can reduce the difficulty of recovery and treatment of the ethylene oxide exhaust gas.

2. The gas liquefaction recovery system is simple to assemble, can be cooperatively used with a sterilizer, can directly perform the compression and liquefaction and gas-liquid separation on the sterilization exhaust gas generated by the sterilizer, and does not require the collection process, the transportation process, and the like, which reduces the difficulty of the recovery and treatment of the ethylene oxide sterilization exhaust gas, and improves the safety of the treatment process.

3. The method for recovering the ethylene oxide sterilization exhaust gas disclosed in the embodiments of the present disclosure has simple operational steps, the ethylene oxide in the sterilization exhaust gas can be liquefied by the high-pressure compression at normal room temperature, and can then be recovered, which allows ethylene oxide to be recovered efficiently, while reducing the recovery costs and protecting the environment.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A method for separating and recovering ethylene oxide, the method comprising:
    transporting a gas to be separated containing ethylene oxide into a gas liquefaction separator through a gas inlet of the gas liquefaction separator by a gas extraction device of a gas liquefaction recovery system;
    pressurizing an inner cavity of a housing of the gas liquefaction separator by a pressurization device to allow the ethylene oxide in the gas to be separated in the gas liquefaction separator to be compressed and liquefied, thereby obtaining a liquid ethylene oxide and a residual gas;
    discharging the residual gas through a gas outlet of the gas liquefaction separator; and
    collecting the liquid ethylene oxide from a liquid outlet of the gas liquefaction separator.

2. The method for separating and recovering ethylene oxide of claim 1, wherein the steps of transporting the gas, pressurizing the inner cavity, and discharging the residual gas are repeated at least once before performing the step of collecting the liquid ethylene oxide.

3. The method for separating and recovering ethylene oxide of claim 1, wherein the steps of transporting the gas, pressurizing the inner cavity, discharging the residual gas, and collecting the liquid ethylene oxide are repeated at least once.

4. The method for separating and recovering ethylene oxide of claim 1, further comprising:
    collecting the liquid ethylene oxide that is discharged through the liquid outlet in a liquid storage tank; and
    collecting the residual gas that is discharged through the gas outlet in a gas storage tank.

5. The method for separating and recovering ethylene oxide of claim 1, wherein an exhaust pipe is mounted in the gas outlet of the gas liquefaction separator and extends into a downstream chamber, and the residual gas is discharged through the exhaust pipe.

6. The method for separating and recovering ethylene oxide of claim 1, wherein a concentration of the ethylene oxide in the gas to be separated ranges from 15% vol to 55% vol; wherein after the step of pressurizing the inner cavity, a gas pressure in the gas liquefaction separator ranges from 0.6 MPa to 0.9 MPa, and a gas temperature in the gas liquefaction separator ranges from 20° C. to 30° C.

7. The method for separating and recovering ethylene oxide of claim 1, wherein the gas to be separated is an ethylene oxide sterilization exhaust gas from an ethylene oxide sterilizer, and the gas extraction device extracts the ethylene oxide sterilization exhaust gas from the ethylene oxide sterilizer into the gas liquefaction separator.

* * * * *